(12) United States Patent
Anderson et al.

(10) Patent No.: US 6,207,857 B1
(45) Date of Patent: Mar. 27, 2001

(54) PRECURSOR COMPOUNDS

(75) Inventors: Denise Anderson, Zurich; Georg Frater, Winterthur, both of (CH)

(73) Assignee: Givaudan-Roure (International) S.A., Geneve (CH)

( * ) Notice: Subject to any disclaimer, the term of this patent is extended or adjusted under 35 U.S.C. 154(b) by 0 days.

(21) Appl. No.: 09/103,034

(22) Filed: Jun. 23, 1998

(30) Foreign Application Priority Data

Jun. 23, 1997 (EP) .............................................. 97 810 398

(51) Int. Cl.[7] .................................................... C07C 69/34
(52) U.S. Cl. .............................. 560/190; 560/64; 560/67; 560/76; 560/81; 560/72; 560/104; 560/105; 560/85; 560/122; 560/127; 560/193; 560/174; 560/254; 554/115; 554/213
(58) Field of Search ..................................... 560/190, 127, 560/76, 81, 254, 193, 105, 67, 85, 64, 72, 104, 122, 174; 554/115, 213

(56) References Cited

U.S. PATENT DOCUMENTS

| | | |
|---|---|---|
| 4,470,421 | 9/1984 | Southwick et al. . |
| 5,531,910 | 7/1996 | Severns et al. . |
| 5,562,847 | 10/1996 | Waite et al. . |
| 5,649,979 | 7/1997 | Paget et al. . |
| 5,726,345 | 3/1998 | Paget et al. . |

FOREIGN PATENT DOCUMENTS

| | | |
|---|---|---|
| 25 17 620 | 11/1976 | (DE) . |
| 6-135891 | 5/1994 | (JP) . |
| 8-502522 | 3/1996 | (JP) . |
| 8-218089 | 8/1996 | (JP) . |
| 9-143194 | 6/1997 | (JP) . |
| WO 95/04809 | 2/1995 | (WO) . |

OTHER PUBLICATIONS

Teruaki Mukaiyama, et al. *Chemistry Letters*, 5:529–32 (1980).
Hashimoto, Shizunobu, *Chemical Abstracts*, 98(19): #160345t (1982).
Derwent Abstract of JP 8–502522 (B2), W. Paget et al., Fragrancing textiles after laundering with a detergent containing lipase–by incorporating a derivative of a fragrant alcohol, aldehyde or ketone into the detergent or subsequent fabric softener (Mar. 19, 1996).

Patent Abstract of Japan of JP 6–135891 (B3), K. Yasuyuki et al., Production of Alkoxyvinyl Ester Derivative (May 17, 1994).
Patent Abstract of Japan of JP 9–143194 (B4), S. Shigeo et al., Polymerizable Sugar Ester And Its Production (Jun. 3, 1997).
Patent Abstract of Japan of JP 8–218089 (B5), I. Takeshi et al., Sustained Release Aroma Composition (Aug. 27, 1996).
Derwent Abstract of DE 25 17 620 (B6), P. Meins et al., Exo–norbornyl acetic acid esters–useful perfume constituents giving fruity or flowery note (Nov. 4, 1976).
Chemical Abstracts, 110: 209208, (1989). V. Bankova et al., On the chemical composition of some propolis fractions with antiviral action.
Chemical Abstracts, 76: 127975, (1972). B.F. Pishnamazzade et al., Plasticization of epoxy resins with different compounds containing reactive functional groups (1972).
Chemical Abstracts, 68: 77919, (1968). I. Kuwajima et al., Reaction of allylmercuric iodide with acyl halide.
Chemical Abstracts, 115: 182596, (1991). V.V. Shchepin et al., Reactions of polyhalo functional compounds with metals and electrophilic reagents. XIII. Reactions of halooxo esters with zinc and acid chlorides.
Chemical Abstracts, 120: 76730, (1994). W.V. Murray et al., The mechanism of formation of 6–aryl–4,6–dioxohexanoic acids from aryl ketones and succinic anhydride.
Chemical Abstracts, 82: 155229, (1975). G.N. Freidlin et al., Technology of the synthesis of divinyl esters of dicarboxylic acids.

*Primary Examiner*—Paul J. Killos
(74) *Attorney, Agent, or Firm*—Mark E. Waddell; Stephen M. Haracz; Bryan Cave LLP

(57) ABSTRACT

The compounds of the formula I

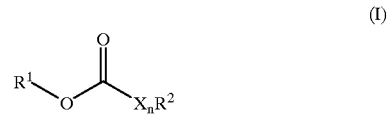

(I)

are precursors for organoleptic and antimicrobial compounds. The latter are generated in the presence of skin bacteria, enzymes or acidic or alkaline conditions. One precursor molecule can provide one or more different compounds.

17 Claims, No Drawings

PRECURSOR COMPOUNDS

FIELD OF THE INVENTION

The present invention relates to a new group of precursors for organoleptic compounds (such as fragrances and masking agents) and antimicrobial compounds.

BACKGROUND OF THE INVENTION

A principal strategy currently employed in imparting odors to consumer products is the admixing of the fragrance directly into the product. There are, however, several drawbacks to this strategy. The fragrance material can be too volatile, resulting in fragrance loss during manufacturing, storage, and use. Many fragrance materials are also unstable over time. This again results in loss during storage.

In many consumer products it is desirable for the fragrance to be released slowly over time. Microencapsulation and inclusion complexes with cyclodextrins have been used to help decrease volatility, improve stability and provide slow-release properties. However, these methods are for a number of reasons often not successful. In addition, cyclodextrins can be too expensive.

Fragrance precursors for scenting fabrics being washed in the presence of a lipase-containing detergents are described in WO 95/04809. The fragrance precursors contained in the detergent and/or in the softener are cleaved by the lipase and a single odoriferous compound, either an odoriferous alcohol or aldehyde or ketone is yielded. Thereby a prolonged scenting effect on the fabric is obtained.

SUMMARY OF THE INVENTION

One object of the present invention is to provide new precursors for compounds with different activities. It is a preferred object of the present invention to provide compounds cleaved under different activating conditions. A further object of the invention is to provide new compounds which are stable under transport and storage conditions. A further object of the present invention is to provide precursor molecules supplying different active compounds simultaneously or successively.

DETAILED DESCRIPTION OF THE INVENTION

The present invention relates to compounds of the formula I

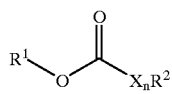

(I)

wherein $R^1$ represents the residue of the enol form of an aldehyde or ketone,

X represents a saturated or unsaturated bivalent hydrocarbon residue with a straight or branched chain with 1 to 20 carbon atoms optionally containing one or more heteroatoms, such as O, N, S and/or P and/or a group —C(O)— and/or substituents of the formula —COOY, —OH, —C=O, or —NH$_2$ and Y is H, a metal atom or $R^4$, and $R^4$ is the rest of an alcohol or phenol $R^4$OH or has the same definition as $R^1$ and is the same or different as $R^1$, $R^2$ represents saturated or unsaturated, substituted or unsubstituted carbocyclic or heterocyclic residue or —COOY, wherein Y is H, a metal atom or $R^3$, and $R^3$ is the rest of an alcohol or phenol or has the same definition as $R^1$ and is the same or different as $R^1$, and $R^2$ can be H if X is substituted by —OH:

n is 0 or 1.

The present invention also includes a compound as defined in formula I which is selected from the group consisting of:

a) succinic acid methyl ester undeca-1,9-dienyl ester;
b) succinic acid 3-(4-tert-butyl-phenyl)-2-methyl-propenyl ester methyl ester;
c) phenyl-acetic acid 2-methyl-undec-1-enyl ester;
d) phenyl-acetic acid undeca-1,9-dienyl ester;
e) phenyl-acetic acid 2,4-dimethyl-cyclohex-3-enylidenemethyl ester;
f) (4-methoxy-phenyl)-acetic acid 3-(4-tert-butyl-phenyl)-2-methyl-propenyl ester;
g) 3-phenyl-propionic acid undeca-1,9-dienyl ester;
h) 3-phenyl-propionic acid 2,4-dimethyl-cyclohex-3-enylidene-methyl ester;
i) 3-phenyl-propionic acid 3-(4-tert-butyl-phenyl)-2-methyl-propenyl ester;
j) 4-methoxy-benzoic acid 2-methyl-undec-1-enyl ester;
k) 4-methoxy-benzoic acid 2,4-dimethyl-cyclohex-3-enylidenemethyl ester;
l) 4-methoxy-benzoic acid 3-(3-isopropyl-phenyl)-but-1-enyl ester;
m) 4-methoxy-benzoic acid undeca-1,9-dienyl ester;
n) succinic acid bis-[3-(4-tert-butyl-phenyl)-2-methyl-propenyl] ester;
o) succinic acid bis-[3-(3-isopropyl-phenyl)-but-1-enyl] ester;
p) succinic acid 3,7-dimethyl-oct-6-enyl ester 3-(isopropyl-phenyl)-but-1-enyl ester;
q) succinic acid 3-(4-tert-butyl-phenyl)-2-methyl-propenyl ester 3,7-dimethyl-oct-6-enyl ester;
r) succinic acid 3,7-dimethyl-oct-6-enyl ester undeca-1,9-dienyl ester;
s) 3-phenyl-acrylic acid 3-(4-tert-butyl-phenyl)-2-methyl-3-phenyl-propenyl ester;
t) succinic acid 3-(3-isopropyl-phenyl)-but-1-enyl ester methyl ester;
u) succinic acid 3-methoxycarbonylmethyl-2-pentyl-cyclopent-1-enyl ester methyl ester;
v) succinic acid 3-(4-isopropyl-phenyl)-2-methyl-propenyl ester methyl ester;
w) phenyl acetic acid 3-(4-isopropyl-phenyl)-2-methyl-propenyl ester;
x) phenyl acetic acid 3-methoxy carbonyl methyl-2-pentyl-cyclopent-1-enyl;
y) phenyl acetic acid 3-(3-isopropyl-phenyl)-but-1-enyl ester;
z) (4-methoxy-phenyl)-acetic acid 3-(3-isopropyl-phenyl)-but-1-enyl ester;
aa) 3-phenyl-propionic acid 3-(3-isopropyl-phenyl)-but-1-enyl ester;
bb) 4-methoxy-benzoic acid 3-(4-tert-butyl-phenyl)-2-methyl-propenyl ester;
cc) succinic acid bis-[3-(4-isopropyl-phenyl)-2-methyl-propenyl] ester;
dd) succinic acid bis-(2,6,10-trimethyl-undeca-1,9-dienyl) ester;
ee) succinic acid bis-(2,6-dimethyl-hepta-1,5-dienyl) ester;
ff) succinic acid bis-[2-(3,7-dimethyl-oct-6-enyloxy)-vinyl] ester;

gg) terephthalic acid bis-[3-(4-tert-butyl-phenyl)-2-methyl-propenyl] ester;
hh) 4-hydroxy-undecanoic acid 3-(4-tert-butyl-phenyl)-2-methyl-propenyl ester;
ii) succinic acid 3,7-dimethyl-octa-2,6-dienyl ester 3-(3-isopropyl-phenyl)-but-1-enyl ester;
jj) succinic acid 3-(3-isopropyl-phenyl)-but-1-enyl ester phenethyl ester;
kk) succinic acid 3-(4-tert-butyl-phenyl)-2-methyl-propenyl ester 3,7-dimethyl-octa-2,6-dienyl ester;
ll) succinic acid 3-(4-tert-butyl-phenyl)-2-methyl-propenyl ester phenethyl ester;
mm) succinic acid 3-(4-tert-butyl-phenyl)-2-methyl-propenyl ester 1,2-dimethyl-4-(2,2,3-trimethyl-cyclopent-3-enyl)-but-3-enyl ester;
nn) succinic acid 3,7-dimethyl-octa-2,6-dienyl ester undeca-1,9-dienyl ester;
oo) succinic acid 3-(4-isopropyl-phenyl)-2-methyl-propenyl ester phenethyl ester;
pp) succinic acid 3,7-dimethyl-oct-6-enyl ester 3-(4-isopropyl-phenyl)-2-methyl-propenyl ester;
qq) succinic acid 3,7-dimethyl-oct-5-enyl ester 2,6,10-trimethyl-undeca-1,9-dienyl ester;
rr) succinic acid 2,6-dimethyl-hepta-1,5-dienyl ester 3,7-dimethyl-octa-2,6-dienyl ester;
ss) succinic acid hex-3-enyl ester 3-methoxycarbonyl-methyl-2-pentyl-cyclopent-1-enyl ester;
tt) succinic acid 3,7-dimethyl-oct-6-enyl ester 3-methoxycarbonyl-methyl-2-pentyl-cyclopent-1-enyl ester; and
uu) phenyl-acetic acid 3-(4-tert-butyl-phenyl)-2-methyl-propenyl ester.

The present invention also relates to personal care and laundry products containing a compound defined by formula I.

The compounds of formula I are not limited to any particular stereoisomers, all possible stereoisomers (E/Z isomers, enantiomers, diastereomers) and all mixtures are thus included within the scope of the invention.

The compounds of formula I are virtually odorless under room temperature, atmospheric conditions and about 20 to 100% relative humidity. However, under activating conditions, they are cleaved and one or more active compounds with organoleptic and/or antimicrobial properties are generated.

The activating conditions which lead to cleavage and the desired active compounds comprise the presence of skin bacteria, especially axilla bacteria, of an enzyme such as protease or lipase, elevated temperature or acidic or alkaline pH-values. The compounds of formula I, upon cleavage, provide aldehydes, ketones, lactones and/or alcohols having organoleptic and/or antimicrobial activity and therefore permit the development of useful consumer products with enhanced organoleptic and/or microbiological properties.

The compounds of the present invention can act as fragrance precursors in personal care products, in laundry products, cleaning compositions, pet care products and environment scents such as air fresheners. They can also act as precursors for odor masking agents in the same products as the fragrance precursors. They also can act as precursors for antimicrobial agents. The fragrance precursors and the precursors for odor masking agents of the invention may be used individually in an amount effective to enhance or to mask the characteristic odor of a material. More commonly, however, the compounds are mixed with other fragrance components in an amount sufficient to provide the desired odor characteristics.

The precursors of formula I provide, upon cleavage, one active compound, if $R^1=R^3$ and X does not yield a different active compound. However, a special advantage of the invention is that one precursor compound can provide also two or more different active compounds, thus enabling to prepare customized solutions for special uses. Two different active compounds are for example provided if $R^1$ and $R^3$ are different or if $R^1=R^3$ and $R^4$ is different or X yields a lactone. Three different active compounds are provided if $R^1$, $R^3$ and $R^4$ are different or if $R^1$ and $R^3$ are different and X yields a lactone.

Compounds of formula II

(II)

will yield one, two or three different active compounds, those of formula III

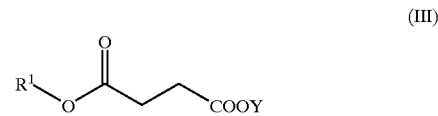

(III)

one or two different active compounds.
Compounds of formula IV

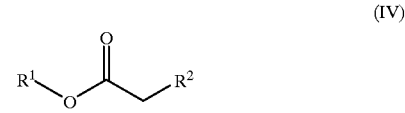

(IV)

wherein $R^1$ has the meaning defined above and $R^2$ represents a saturated or unsaturated, substituted or unsubstituted carbocyclic or heterocyclic residue, will preferably yield two different active compounds.

Compounds of formula V

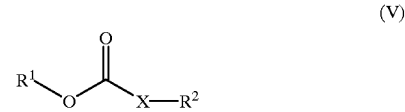

(V)

wherein X is substituted by —OH and $R^2$ is H yield two different active compounds one of which is a lactone.

Due to the in situ generation of the active compounds the desired effect is prolonged and the substantivity on different substrates is enhanced. If two or more active compounds are provided, they can be generated, depending on the precursor and/or the activating conditions, simultaneously or successively. Further, the precursors of the invention provide slow release of the active compounds.

Examples of aldehydes $R^1HO$ and $R^3HO$ and $R^4HO$ include:

2,6,10-trimethylundec-9-enal*; 1,2,3,4,5,6,7,8,-octahydro-8,8-dimethyl-2-napthalenecarboxaldehyde; tridecanal; 2-[4-(1-methylethyl)phenyl]-ethanal; 2,4-dimethyl-cyclohex-3-ene-1-carbox-aldehyde*; 4-carbox-aldehyde-1,3,5-trimethyl-cyclohex-1-ene*; 1-carboxalde-hyde-2,4-dimethyl-cyclohex-3-ene*; 1-carboxaldehyde-4-(4-hydroxy-4-methylpentyl)-cyclohex-3-ene*; 3,5,5-trimethyl-hexanal; heptanal*; 2,6-dimethyl-hept-5-enal*; decanal**;

dec-9-enal; dec-4-en-1-al; 2-methyldecanal*; undec-10-ene-1-al**; undecanal*; dodecanal; 2-methyl-undecanal; tridecanal; octanal**; nonanal*; 3,5,5-trimethylhexanal; undec-9-eneal**; 2-phenyl-propanal*; 4-methyl-phenyl acet-aldehyde*; 3,7-dimethyl-octanal*; dihydrofarnesal**; 7-hydroxy-3,7-dimethyl -octanal*; 2,6-dimethyl-oct-5-ene-1-al; 2-(4,-(1-methylethyl)phenyl)-ethanal*; 3-(3-isopropyl-phenyl)-butanal**; 2-(3,7-dimethyoct-6-en-oxy)-ethanal; 1-carboxaldehyde-4-(4-methyl-3-penten-1-ly)-cyclohex-3-ene*; 2,3,5,5,-tetramethyl-hexanal; longifolic aldehyde; 2-methyl-4-(2,6,6-trimethylcyclohex-2-en-1-yl)-butanal*; 2-methyl-3-(4-tert-butylphenyl)propanal**; 4-(1,1-dimethyl-ethyl)-benzenepropanal*; 2-[4-(1-methyl-ethyl) phenyl]-propanal; alpha-methyl-1,3-benzodioxole-5-propanal*; 3,7-dimethyl-oct-6-en-1-al*; 2-methyl-3-(p-isopropylphenyl)-propionaldehyde*; 4-(4-hydroxy-4-methyl-pentyl)-cyclohex-3-en-1-carboxaldehyde**; alpha-methyl-1,3-benzodioxole-5-propanal*; 1-carboxaldehyde-4-(1,1-dimethylethyl)-cyclo-hexane; 4-(octahydro-4,7-methano-5H-inden-5-ylidene)-butanal; [(3,7-dimethyl-6-octenyl)oxy]-acetaldehyde** whereby * indicates the preferred aldehydes and ** indicate the more preferred aldehydes.

Examples of ketones $R^1O$, $R^3O$ and $R^4O$ include:

2-heptyl-cyclopentanone; 2,2,6,10-tetrametyltricyclo-[5.4.0.0(6,10)]-undecan-4-one; benzylacetone*; carvone*; 1,2,3,5,6,7-hexahydro-1,1,2,3,3,-pentamentyl-4H-inden-4-one*; methyl heptenone*; dimethyl octenone*; 2-(butan-2-yl)-cyclohexanone*; 2-hexyl-cyclopent-2-en-1-one*; 2-(1-methylethyl)- 5-methyl-cyclohexanone*; 2-(2-methylethyl)-5-methyl-cyclohexanone*; 3-methyl-cyclopentadecanone; 4-tert-pentyl-cyclohexanone*; 3-oxo-2-pentyl-cyclopentane-acetic acid methyl ester**; 1-(1,2,3,4,5,6,7,8-octahydro-2,3,8,8-tetramethyl-2-naphthalenyl)-ethanone*; 3-methyl-5-propyl-cyclohex-2-en-1-one* whereby * indicates the preferred ketones and ** indicate the more preferred ketones.

Examples of alcohols $R^3OH$ and $R^4OH$ are primary, secondary and tertiary alcohols and phenols such as:

amyl alcohol; hexyl alcohol*; 2-hexyl alcohol*; heptyl alcohol*; octyl alcohol*; nonyl alcohol*; decyl alcohol*; undecyl alcohol*; lauryl alcohol*; myristic alcohol; 3-methyl-but-2-en-1-ol*; 3-methyl-1-pentanol; cis-3-hexenol*; cis-4-hexenol*; 3,5,5-trimethyl hexanol; 3,4,5,6,6-pentamethylheptan-2-ol*; citronellol*; geraniol*; oct-1-en-3-ol; 2,5,7-trimethyl octan-3-ol; 2-cis-3,7-dimethyl-2,6-octadien-1-ol; 6-ethyl-3-methyl-5-octen-1-ol*; 3,7-dimethyl-oct-3,6-dienol*; 3,7-dimethyloctanol*; 7-methoxy-3,7-dimethyl-octan-2-ol*; cis-6-nonenol*; 5-ethyl-2-nonanol; 6,8-dimethyl-2-nonanol*; 2,2,8-trimethyl-7(8)-nonene-3-ol; nona-2,6-dien-1-ol; 4-methyl-3-decen-5-ol*; dec-9-en-1-ol; benzylalcohol; 2-methyl undecanol; 10-undecen-1-ol; 1-phenyl ethanol*; 2-phenyl ethanol*; 2-methyl-3-phenyl-3-propenol; 2-phenyl propanol*; 3-phenyl propanol*; 4-phenyl-2-butanol; 2-methyl-5-phenyl pentanol*; 2-methyl-4-phenyl-pentanol*; 3-methyl-5-phenyl-pentanol*; 2-(2-methylphenyl)-ethanol*; 4-(1-methylethyl)benzene methanol; 4-(4-hydroxyphenyl)-butan-2-one*; 2-phenoxy ethanol*; 4-(1-methylethyl)-2-hydroxy-1-methyl benzene; 2-methoxy-4-methyl phenol; 4-methyl phenol; anisic alcohol*; p-tolyl alcohol*; cinnamic alcohol*; vanillin*; ethyl vanillin*; eugenol*; isoeugenol*; thymol; anethol*; decahydro 2-naphthalenol; borneol*; cedrenol*; farnesol*; fenchyl alcohol*; menthol*; 3,7,11-trimethyl-2,6,10-dodecatrien-1-ol; alpha ionol*; tetrahydro ionol*; 2-(1,1-dimethylethyl)-cyclohexanol*; 3-(1,1-dimethylethyl)cyclohexanol*; 4-(1,1-dimethylethyl)cyclohexanol*; 4-isopropyl cyclohexanol*; 6,6-dimethyl-bicyclo [3.3.1]hept-2-ene-2-ethanol; 6,6-dimethyl-bicyclo[3.1.1]hept-2-ene-methanol*; p-menth-8-en-3-ol*; 3,3,5-trimethyl cyclohexanol; 2,4,6-trimethyl-3-cyclohexenyl-methanol*; 4-(1-methylethyl)cyclohexyl-methanol*; 4-(1,1-dimethylethyl)cyclohexanol; 2-(1,1-dimethylethyl)-cyclohexanol; 2,2,6-trimethyl-alpha-propyl cyclohexane propanol*; 5-(2,2,3-trimethyl-3-cyclo-pentenyl)-3-methylpentan-2-ol*; 3-methyl-5-(2,2,3-trimethylcyclopentyl-3-enyl)pent-4-en-2-ol*; 2-ethyl-4(2,2,3-trimethylcyclopentyl-3-enyl)but-2-en-1-ol*; 4-(5,5,6-trimethylbicyclo[2.2.1]hept-2-yl)-cyclohexanol*; 2-(2-methylpropyl)-4-hydroxy-4-methyl-tetrahydropyran*; 2-cyclohexyl propanol*; 2-(1,1-dimethylethyl)-4-methyl cyclohexanol*; 1-(2-tert-butyl-cyclohexyloxy)-2-butanol*; 1-(4-isoporpyl-cyclohexyl)-ethanol*; 1-(4-hydroxyphenyl)-butan-3-one; 2,6-dimethyl-oct-7-en-2-ol*; 2,6-dimethyl-heptan-2-ol*; 3,7-dimethyl-octa-1,6-dien-3-ol* etc.

* indicates preferred alcohols

Examples of lactones derived from X substituted by —OH when $R^2$=H in formula I include:

6-methyl-pyran-2-one; 5-heptydihydro-2(3H)-furanone*; 5-pentyldihydro-2(3H)-furanone*; 5-(3-hexenyl)dihydro-5-methyl-(Z)-2(3H)-furanone; 5-hexyldihydro-5-methyl-2(3H)-furanone; 5-hexyldihydro-2(3H)-furanone*; 5-octyldihydro-2(3H)-furanone; 8-(1-methylethyl)-1-oxaspiro [4.5]-decan-2-one*; 8-methyl-1-oxaspiro[4.5]-decan-2-one; 8-ethyl-1-oxaspiro[4.5]-decan-2-one; 5-(1,5-dimethyl-4-hexenyl)-dihydro-2(3H)-furanone; 2-oxo-5-butyl-tetrahydrofuran*; 4-methyl-5-pentyl-dihydro-2(3H)-furan-2-one; 5 -hexyldihydro-5-methyl-2(3H)-furanone; dihydro-5-methyl-5-vinyl-2(3H)-furanone; octahydro-2H-1-benzopyran-2-one; tetrahydro-6-pentyl-2H-pyran-2-one; tetrahydro-6-hexyl-2H-pyran-2-one; tetrahydro-6-heptyl-2H-pyran-2-one; tetrahydro-6-(3-pentenyl)-(E)-2H-pyran-2-one; tetrahydro-6-(2-pentenyl)-(Z)-2H-pyran-2-one whereby * indicates the preferred lactones.

The foregoing is not intended to be a complete list of the organoleptic especially odoriferous and/or antimicrobial aldehydes, ketones, lactones alcohols and phenols which are generated as a result of the desired cleavage of the compounds of formula I by skin bacteria, by enzymes, by elevated temperatures or by acidic and/or alkaline pH-values. The skilled person is, however, quite aware of those aldehydes, ketones, lactones and alcohols which provide the desired organoleptic, e.g. fragrance and odor masking and/or antimicrobial effects.

The compounds of formula I may preferably be used as sustained release odorants but also to mask or attenuate undesirable odors or to provide additional odors not initially present in consumer products, i.e. personal care products such as cosmetic products destined for application to human skin such as underarm deodorants or antiperspirants or other deodorants contacting the body, or in hand lotions, baby powders, baby lotions, ointments, foot products, facial cleansers, body wipes, facial make-up, colognes, after-shave lotions, shaving creams, etc. Additional applications include laundry detergents, fabric softeners, fabric softener sheets, (automatic) dishwasher detergents, and other enzyme-containing consumer products. Further applications are air fresheners and odorants, odor masking agents and/or antimicrobial agents.

The amount required to produce the desired, overall effect varies depending upon the particular compounds of formula I chosen, the product in which it will be used, and the particular effect desired.

For example, depending upon the selection and concentration of the compound chosen, when a compound of the formula I is added either singly or as a mixture, e.g. to a deodorant or laundry product composition at levels ranging from about 0.1 to about 10% by weight, or most preferred about 0.25 to about 4% by weight, an odorant, i.e. an odoriferous, aldehyde, ketone, alcohol or lactone in an "organoleptically effective amount" is released when the product is used. This newly formed odorant serves to enhance the odor of the product itself or of a fragrance present in the product.

As is evident from the above compilation of aldehydes, ketones, alcohols and lactones, a broad range of known odorants or odorant mixtures can be generated from precursors of the invention. While manufacturing compositions the precursors of the invention may be used according to methods known to the perfumer, such as e.g. from W. A. Poucher, Perfumes, Cosmetics, Soaps, 2, 7th Edition, Chapman and Hall, London 1974.

The compounds of formula I can be prepared by using standard methods known to the skilled chemist. Enol esters of the general formula I may be prepared using the procedure of J. Chem. Soc., Perkin Trans. I, 2509 (1993).

Convenient methods are outlined in the Examples without limiting the invention thereto.

EXAMPLE 1 a) Acetic acid 3-(4-tert-butyl-phenyl)-2-methyl-propenyl ester

A solution of 200 g 2-methyl-3-(4-tert-butylphenyl) propanal, 280 ml triethylamine and 13.4 g sodium acetate in 800 ml of acetic anhydride was stirred at 120° C. for 5.5 hours. Then the solution was cooled, water was added and the water phase was extracted with hexane. The organic phase was washed with 2N NaOH and water to neutrality, dried and evaporated to dryness. The residue was distilled to yield 185 g of a colorless liquid.

NMR (CDCl$_3$) δ 7.35–6.97 (m, 5H), 3.43+3.21 (s, 2H, E/Z), 2.13 (s, 3H), 1.60 (s, 3H), 1.30 (s, 9H) ppm.

b) Acetic acid undeca-1,9-dienyl ester

According to the procedure of Example 1, acetic acid undeca-1,9-dienyl ester was prepared from undec-9-enal, acetic anhydride, sodium acetate and triethylamine.

c) Acetic acid 2-methyl-undec-1-enyl ester

According to the same procedure, acetic acid 2-methyl-undec-1-enyl ester was prepared from 2-methyl-undecanal, acetic anhydride, sodium acetate and triethylamine.

d) Acetic acid 2,4-dimethyl-cyclohex-3-enylidenemethyl ester

According to the same procedure, acetic acid 2,4-dimethyl-cyclohex-3-enylidenemethyl ester was prepared from 1-carboxyaldehyde-3,5-dimethyl cyclohex-3-ene, acetic anhydride, sodium acetate and triethylamine.

e) Acetic acid 3-(3-isopropyl-phenyl)-but-1-enyl ester

According to the same procedure acetic acid 3-(3-isopropyl-phenyl)-but-1-enyl ester was prepared from 3-(3-isopropylphenyl)butanal, acetic anhydride, sodium acetate and triethylamine.

f) Acetic acid 3-(4-isopropyl-phenyl)-2-methyl-propenyl ester

According to the same procedure, acetic acid 3-(4-isopropyl-phenyl)-2-methyl-propenyl ester was prepared from 2-methyl-3-(4-isopropyl-phenyl)-propionaldehyde, acetic anhydride, sodium acetate and triethylamine.

g) Acetic acid 2,6-dimethyl-hepa-1,5-dienyl ester

According to the same procedure, acetic acid 2,6-dimethyl-hepa-1,5-dienyl ester was prepared from 2,6-dimethyl-hept-5-enal, acetic anhydride, sodium acetate and triethylamine.

h) Acetic acid 2,6,10-trimethyl-undeca-1,9-dienyl ester

According to the same procedure, acetic acid 2,6,10-trimethyl-undeca-1,9-dienyl ester was prepared from 2,6,10-trimethylundec-9-enal, acetic anhydride, sodium acetate and triethylamine.

i) Acetic acid 2-(3,7-dimethyl-oct-6-enyloxy)-vinyl ester

According to the same procedure, acetic acid 2-(3,7-dimethyl-oct-6-enyloxy)-vinyl ester was prepared from [(3,7-dimethyl- 6-octenyl)oxy]-acetaldehyde, acetic anhydride, sodium acetate and triethylamine.

EXAMPLE 2 a) 3-Phenyl-propionic acid 3-(4-tert-butyl-phenyl)-2-methyl-propenyl ester

A solution of 65.8 g acetic acid 3-(4-tert-butyl-phenyl)-2-methyl-propenyl ester in 200 ml of THF was cooled to −70° C. A solution of 42.3 g potassium-tert-butoxide in 200 ml of THF was added at −70° C. during 20 min. and the resulting reaction mixture was stirred for 90 min. at the same temperature. 53.5 g 3-phenyl-propionyl chloride was dropped in and the reaction mixture was stirred for another 3 hours at −70° C. Then the reaction mixture was diluted with ether, washed with saturated NaHCO$_3$ and brine. The organic phase was dried, filtered and evaporated to dryness. The residue was thin-layer distilled to yield 75.0 g of a yellow oil.

NMR (CDCl$_3$) δ 7.33–7.04 (m, 9H+1H), 3.03–2.95 (t, 2H), 2.77–2.67 (m, 2H), 1.58–1.56 (t, 3H), 1.30 (s, 9H) ppm.

b) Succinic acid bis-[3-(4-tert-butyl-phenyl)-2-methyl-propenyl] ester

According to the same procedure, succinic acid bis-[3-(4-tert-butyl-phenyl)-2-methyl-propenyl] ester was prepared from acetic acid 3-(4-tert-butyl-phenyl)-2-methyl-propenyl ester, succinyl chloride and potassium-tert-butoxide.

c) (4-Methoxy-phenyl)-acetic acid 3-(4-tert-butyl-phenyl)-2-methyl-propenyl ester According to the same procedure, (4-methoxy-phenyl)-acetic acid 3-(4-tert-butyl-phenyl)-2-methyl-propenyl ester was prepared from acetic acid 3-(4-tert-butyl-phenyl)-2-methyl-propenyl ester, 4-methoxyphenylacetyl chloride and potassium-tert-butoxide.

d) Succinic acid 3-(4-tert-butyl-phenyl)-2-methyl-propenyl ester methyl ester According to the same procedure, succinic acid 3-(4-tert-butyl-phenyl)-2-methyl-propenyl ester methyl ester was prepared from acetic acid 3-(4-tert-butyl-phenyl)-2-methyl-propenyl ester, 3-carbomethoxy-propionyl chloride and potassium-tert-butoxide.

e) Succinic acid methyl ester undeca-1,9-dienyl ester

According to the same procedure, succinic acid methyl ester undeca-1,9-dienyl ester was prepared from acetic acid undeca-1,9-dienyl ester, 3-carbomethoxy propionyl chloride and potassium-tert-butoxide.

f) Succinic acid bis-[3-(3-isopropyl-phenyl)-but-1-enyl] ester

According to the same procedure, succinic acid bis-[3-(3-isopropyl-phenyl)-but-1-enyl] ester was prepared from acetic acid 3-(3-isopropyl-phenyl)-but-1-enyl ester, 3-carbomethoxy propionyl chloride and potassium-tert-butoxide.

g) Phenyl-acetic acid undeca-1,9-dienyl ester

According to the same procedure, phenyl-acetic acid undeca-1,9-dienyl ester was prepared from acetic acid undeca-1,9-dienyl ester, phenylacetyl chloride and potassium-tert-butoxide.

h) Phenyl-acetic acid 3-(4-tert-butyl-phenyl)-2-methyl-propenyl ester

According to the same procedure, phenyl-acetic acid 3-(4-tert-butyl-phenyl)-2-methyl-propenyl ester was prepared from acetic acid 3(-4-tert-butyl-phenyl)-2-methyl-propenyl ester, phenylacetyl chloride and potassium-tert-butoxide.

i) Phenyl-acetic acid 2-methyl-undec-1-enyl ester

According to the same procedure, phenyl-acetic acid 2-methyl-undec-1-enyl ester was prepared from acetic acid 2-methyl-undec-1-enyl ester, phenylacetyl chloride and potassium-tert-butoxide.

j) Phenyl-acetic acid 2,4-dimethyl-cyclohex-3-enylidenemethyl ester

According to the same procedure, phenyl-acetic acid 2,4-dimethyl-cyclohex-3-enylidenemethyl ester was prepared from acetic acid 2,4-dimethyl-cyclohex-3-enylidenemethyl ester, phenylacetyl chloride and potassium-tert-butoxide.

k) 4-Methoxy-benzoic acid undeca-1,9-dienyl ester

According to the same procedure, 4-methoxy-benzoic acid undeca-1,9-dienyl ester was prepared from acetic acid undeca- 1,9-dienyl ester, p-anisoyl chloride and potassium-tert-butoxide.

l) 4-Methoxy-benzoic acid 2,4-dimethyl-cyclohex-3-enylidenemethyl ester

According to the same procedure, 4-methoxy-benzoic acid 2,4-dimethyl-cyclohex-3-enylidenemethyl ester was prepared from acetic acid 2,4-dimethyl-cyclohex-3-enylidenemethyl ester, p-anisoyl chloride and potassium-tert-butoxide.

m) 4-Methoxy-benzoic acid 2-methyl-undec-1-enyl ester

According to the same procedure, 4-methoxy-benzoic acid 2-methyl-undec-1-enyl ester was prepared from acetic acid 2-methyl-undec-1-enyl ester, p-anisoyl chloride and potassium-tert-butoxide.

n) 4-Methoxy-benzoic acid 3-(3-isopropyl-phenyl)-but-1-enyl ester

According to the same procedure, 4-methoxy-benzoic acid 3-(3-isopropyl-phenyl)-but-1-enyl ester was prepared from acetic acid 3-(3-isopropyl-phenyl)-but-1-enyl ester, p-anisoyl chloride, and potassium-ter-butoxide.

o) 3-Phenyl-propionic acid 2,4-dimethyl-cyclohex-3-enylidene-methyl ester

According to the same procedure, 3-phenyl-propionic acid 2,4-dimethyl-cyclohex-3-enylidene-methyl ester was prepared from acetic acid 2,4-dimethyl-cyclohex-3-enylidenemethyl ester, 3-phenyl-propionyl chloride and potassium-tert-butoxide.

p) 3-Phenyl-propionic acid undeca-1,9-dienyl ester

According to the same procedure, 3-phenyl-propionic acid undeca-1,9-dienyl ester was prepared from acetic acid undeca-1,9-dienyl ester, 3-phenyl-propionyl chloride and potassium-tert-butoxide.

q) 3-Phenyl-acrylic acid 3-(4-tert-butyl-phenyl)-2-methyl-propenyl ester

According to the same procedure, 3-phenyl-acrylic acid 3-(4-tert-butyl-phenyl)-2-methyl-propenyl ester (an antimicrobial precursor) was prepared from acetic acid 3-(4-tert-butyl-phenyl)-2-methyl-propenyl ester and cinnamoyl chloride.

r) Succinic acid 3-(3-isopropyl-phenyl)-but-1-enyl ester methyl ester

According to the same procedure, succinic acid 3-(3-isopropyl-phenyl)-but-1-enyl ester methyl ester was prepared from acetic acid 3-(3-isopropyl-phenyl)-but-1-enyl ester, 3-carbomethoxy propionyl chloride and potassium tert-butoxide.

s) Succinic acid 3-methoxycarbonylmethyl-2-pentyl-cyclopent-1-enyl ester methyl ester According to the same procedure, succinic acid 3-methoxycarbonylmethyl-2-pentyl-cyclopent-1-enyl ester methyl ester was prepared from 2-oxo-1-pentyl-cyclopentane acetic acid methyl ester, 3-carbomethoxy propionyl chloride and potassium tert-butoxide.

t) Succinic acid 3-(4-isopropyl-phenyl)-2-methyl-propenyl ester methyl ester According to the same procedure, succinic acid 3-(4-isopropyl-phenyl)-2-methyl-propenyl ester methyl ester was prepared from acetic acid 3-(4-isopropyl-phenyl)-2-methyl-propenyl ester, 3-carbomethoxy propionyl chloride and potassium tert-butoxide.

u) Phenyl acetic acid 3-(4-isopropyl-phenyl)-2-methyl-propenyl ester

According to the same procedure, phenyl acetic acid 3-(4-isopropyl-phenyl)-2-methyl-propenyl ester was prepared from acetic acid 3-(4-isopropyl-phenyl)-2-methyl-propenyl ester, phenylacetyl chloride and potassium tert-butoxide.

v) Phenyl acetic acid 3-methoxy carbonyl methyl-2-pentyl-cyclopent-1-enyl ester According to the same procedure, phenyl acetic acid 3-methoxy carbonyl methyl-2-pentyl-cyclopent-1-enyl ester was prepared from 3-oxo-2-pentyl-cyclopentane acetic acid methyl ester, phenylacetyl chloride and potassium tert-butoxide.

w) Phenyl acetic acid 3-(3-isopropyl-phenyl)-but-1-enyl ester

According to the same procedure, phenyl acetic acid 3-(3-isopropyl-phenyl)-but-1-enyl ester was prepared from acetic acid 3-(3-isopropyl-phenyl)-but-1-enyl ester, phenylacetyl chloride and potassium tert-butoxide.

x) (4-Methoxy-phenyl)-acetic acid 3-(3-isopropyl-phenyl)-but-1-enyl ester

According to the same procedure, (4-methoxy-phenyl)-acetic acid 3-(3-isopropyl-phenyl)-but-1-enyl ester was prepared from acetic acid 3-(4-isopropyl-phenyl)-2-methyl-propenyl ester, 4-methoxyphenylacetyl chloride and potassium tert-butoxide.

y) 3-Phenyl-propionic acid 3-(3-isopropyl-phenyl)-but-1-enyl ester

According to the same procedure, 3-phenyl-propionic acid 3-(3-isopropyl-phenyl)-but-1-enyl ester was prepared from acetic acid 3-(3-isopropyl-phenyl)-but-1-enyl ester, hydrocinnamoyl chloride and potassium tert-butoxide.

z) 4-Methoxy-benzoic acid 3-(4-tert-butyl-phenyl)-2-methyl-propenyl ester

According to the same procedure, 4-methoxy-benzoic acid 3-(4-tert-butyl-phenyl)-2-methyl-propenyl ester was prepared from acetic acid 3-(4-tert-butyl-phenyl)-2-methyl-propenyl ester, p-anisoyl chloride and potassium tert-butoxide.

aa) Succinic acid bis-[3-(4-isopropyl-phenyl)-2-methyl-propenyl] ester

According to the same procedure, succinic acid bis-[3-(4-isopropyl-phenyl)-2-methyl-propenyl] ester was prepared from acetic acid 3-(4-isopropyl-phenyl)-2-methyl-propenyl ester, succinyl chloride and potassium tert-butoxide.

bb) Succinic acid bis-(2,6,10-trimethyl-undeca-1,9-dienyl) ester

According to the same procedure, succinic acid bis-(2,6,10-trimethyl-undeca-1,9-dienyl) ester was prepared from acetic acid 2,6,10-trimethyl-undeca-1,9-dienyl ester, succinyl chloride and potassium tert-butoxide.

cc) Succinic acid bis-(2,6-dimethyl-hepta-1,5-dienyl) ester

According to the same procedure, succinic acid bis-(2,6-dimethyl-hepta-1,5-dienyl) ester was prepared from acetic acid 2,6-dimethyl-hepta-1,5-dienyl ester, succinyl chloride and potassium tert-butoxide.

dd) Succinic acid bis-[2-(3,7-dimethyl-oct-6-enyloxy)-vinyl] ester

According to the same procedure, succinic acid bis-[2-(3,7-dimethyl-oct-6-enyloxy)-vinyl] ester was prepared from acetic acid 2-(3,7-dimethyl-oct-6-enyloxy)-vinyl ester, succinyl chloride and potassium tert-butoxide.

ee) Terephthalic acid bis-[3-(4-tert-butyl-phenyl)-2-methyl-propenyl] ester According to the same procedure, terephthalic acid bis-[3-(4-tert-butyl-phenyl)-2-methyl-propenyl] ester was prepared from acetic acid 3-(4-tert-butyl-phenyl)-2-methyl-propenyl ester, terephthaloyl chloride and potassium tert-butoxide.

EXAMPLE 3 a) 4-Oxo-undecanoic acid 3-(4-tert-butyl-phenyl)-2-methyl-propenyl ester

A solution of 43.79 g acetic acid 3-(4-tert-butyl-phenyl)-2-methyl-propenyl ester in 200 ml of THF was cooled to −70° C. A solution of 27.16 g potassium-tert-butoxide in 200 ml of THF was added at −70° C. during 20 min. and the resulting reaction mixture was stirred for 90 min. at the same temperature. Then a solution of 53.00 g 4-oxo-undecanoyl chloride in 200 ml of THF was dropped in and the reaction mixture was stirred for another 2.5 hours at −70° C. Then the reaction mixture was diluted with ether, washed with saturated $NaHCO_3$ and brine. The organic phase was dried, filtered and evaporated to dryness. The residue was thin-layer distilled and purified by chromatography to yield 25.73 g of a yellow oil.

NMR ($CDCl_3$) δ 7.37–7.06 (m, 4H), 7.02+6.98 (s, 1H, E/Z),3.42+3.22 (s,2H, E/Z), 2.82–2.62 (m, 4H),2.51–2.39 (t, 2H),1.69–1.50 (m, 5H), 1.44–1.15 (m, 17H), 0.96–0.80 (t, 3H) ppm.

b) 4-Hydroxy-undecanoic acid 3-(4-tert-butyl-phenyl)-2-methyl-propenyl ester A solution of 10.00 g 4-oxo-undecanoic acid 3-(4-tert-butyl-phenyl)-2-methyl-propenyl ester was dissolved in 60 ml methanol and a trace of bromocresol green was added. When 1.63 g sodium borohydride was added, the color changed immediately from yellow to deep blue. Several drops of 2N HCl/methanol solution turned the color of the reaction back to yellow. The reaction was stirred for 2½ hours, with occasional addition of acid to maintain the yellow color. The reaction mixture was evaporated to dryness and water was added to the residue. This solution was extracted with ether and washed with water. The solution was dried, filtered and evaporated to dryness to yield 10.07 g of a colorless oil.

NMR ($CDCl_3$) δ 7.35–7.25 (m, 2H), 7.15–7.03 (m, 3H), 3.72–3.57 (m, 1H), 3.27+3.2 (s, 2H, E/Z), 2.62–2.5 (m,4H), 2.5–2.4 (m, 2H), 1.65–1.56 (m, 5H), 1.35–1.21 (m, 17H), 0.95–0.82 (m, 3H).

EXAMPLE 4 a) Succinic acid mono-(3,7-dimethyl-oct-6-enyl) ester

A solution of 30.0 g succinic anhydride, 46.9 g citronellol, 36.0 g pyridine and 2.2 g 4-dimethylaminopyridine in 300 ml of dichloromethane was refluxed for 22 hours. Then the solution was cooled, ether was added and the organic phase was washed with 2N HCl and water to neutrality, dried and evaporated to dryness. The residue was wipe-film distilled to yield 36.4 g of a colorless liquid.

NMR ($CDCl_3$) δ 10.0 (s, 1H), 5.08 (t, 1H), 4.13 (t, 2H), 2.75–2.54 (m, 4H), 2.08–1.88 (m, 2H), 1.69 (s, 3H), 1.60 (s, 3H), 1.80–1.00 (m, 5H), 0.91 (d, 3H) ppm.

b) Succinic acid monophenethyl ester

According to the same procedure, succinic acid monophenethyl ester was prepared from phenethyl alcohol and succinic anhydride.

c) Succinic acid mon-(3,7-dimethyl-octa-2,6-dienyl) ester

According to the same procedure, succinic acid mon-(3,7-dimethyl-octa-2,6-dienyl) ester was prepared from geraniol and succinic anhydride.

d) Succinic acid mono-[1,2-dimethyl-4-(2,2,3-trimethyl-cyclopent-3-enyl)-but-3-enyl] ester According to the same procedure, succinic acid mono-[1,2-dimethyl-4-(2,2,3-trimethyl-cyclopent-3-enyl)-but-3-enyl] ester was prepared from 3-methyl-5-(2,2,3-trimethyl-3-cyclopenten-1-yl)-4-penten-2-ol and succinic anhydride.

e) Succinic acid mono(hex-3-enyl) ester

According to the same procedure, succinic acid mono(hex-3-enyl) ester was prepared from cis-3-hexenol and succinic anhydride.

EXAMPLE 5 a) 3-Chlorocarbonyl-propionic acid 3,7-dimethyl-oct-6-enyl ester

A solution of 35.5 g succinic acid mono-(3,7-dimethyl-oct-6-enyl) ester and 12.3 g pyridine in 200 ml of ether was cooled in an ice bath. Then a solution of 18.0 g thionyl chloride in 100 ml of ether was added dropwise at 5–10° C. during 90 min. The resulting solution was stirred overnight at room temperature, then it was filtered and evaporated to dryness. The residue was not further purified to yield 31.5 g of a yellow liquid.

NMR (CDCl$_3$) δ 5.08 (t, 1H), 4.13 (t, 2H), 3.21 (t, 2H), 2.64 (t, 3H), 2.10–1.87 (m, 2H), 1.68 (s, 3H), 1.60 (s, 3H), 1.80–1.05 (m, 5H), 0.91 (d, 3H) ppm.

b) 3-Chlorocarbonyl-propionic acid 3,7-dimethyl-oct-2,6-dienyl ester

According to the same procedure, 3-chlorocarbonyl-propionic acid 3,7-dimethyl-oct-2,6-dienyl ester was prepared from succinic acid mon-(3,7-dimethyl-octa-2,6-dienyl) ester and thionyl chloride.

c) 3-Chlorocarbonyl-propionic acid phenethyl ester

According to the same procedure, 3-chlorocarbonyl-propionic acid phenethyl ester was prepared from succinic acid monophenethyl ester and thionyl chloride.

d) 3-Chlorocarbonyl-propionic acid 1,2-dimethyl4-(2,2,3-trimethyl-cyclopent-3-enyl)-but-3-enyl ester According to the same procedure, 3-chlorocarbonyl-propionic acid 1,2-dimethyl4-(2,2,3-trimethyl-cyclopent-3-enyl)-but-3-enyl ester was prepared from succinic acid mono-[1,2-dimethyl-4-(2,2,3-trimethyl-cyclopent-3-enyl)-but-3-enyl] ester and thionyl chloride.

e) 3-Chlorocarbonyl-propionic acid hex-3-enyl ester

According to the same procedure, 3-chlorocarbonyl-propionic acid hex-3-enyl ester was prepared from succinic acid mono(hex-3-enyl) ester and thionyl chloride.

EXAMPLE 6 a) Succinic acid 3,7-dimethyl-oct-6-enyl ester 3-(3-isopropyl-phenyl)-but-1-enyl ester A solution of 7.60 g acetic acid 3-(3-isopropyl-phenyl)-but-1-enyl ester in 50 ml of THF was cooled to −70° C. A solution of 5.00 g potassium-tert-butoxide in 50 ml of THF was added at 70° C. and the resulting reaction mixture was stirred for 2 hours at the same temperature. 11.20 g 3-chlorocarbonyl-propionic acid 3,7-dimethyl-oct-6-enyl ester was then dropped in and the reaction mixture was stirred for another 2 hours at −70° C. Then the reaction mixture was diluted with ether, washed with saturated NaHCO3 and brine. The organic phase was dried, filtered and evaporated to dryness. The residue was purified by chromatography to yield 7.10 g of a yellow oil.

NMR (CDCl$_3$) δ 7.30–6.93 (m, 5H), 5.71–5.55 (m, 1H), 5.08 (t, 1H), 4.13 (t, 2H), 3.57–3.40 (m, 1H), 2.99–2.80 (m, 1H), 2.80–2.55 (m, 4H), 2.09–1.87 (m, 2H), 1.70 (s, 3H), 1.60 (s, 3H), 1.70–1.00 (m, 8H), 1.26 (s, 3H), 1.21 (s, 3H), 0.90 (d, 3H) ppm.

b) Succinic acid 3-(4-tert-butyl-phenyl)-2-methyl-propenyl ester 3,7-dimethyl-oct-6-enyl ester According to the same procedure, succinic acid 3-(4-tert-butyl-phenyl)-2-methyl-propenyl ester 3,7-dimethyl-oct-6-enyl ester was prepared from acetic acid 3-(4-tert-butyl-phenyl)-2-methyl-propenyl ester, 3-chlorocarbonyl-propionic acid 3,7-dimethyl-oct-6-enyl ester and potassium-tert-butoxide.

c) Succinic acid 3,7-dimethyl-oct-6-enyl ester undeca-1,9-dienyl ester

According to the same procedure, succinic acid 3,7-dimethyl-oct-6-enyl ester undeca-1,9-dienyl ester was prepared from acetic acid undeca-1,9-dienyl ester, 3-chlorocarbonyl-propionic acid 3,7-dimethyl-oct-6-enyl ester and potassium-tert-butoxide.

d) Succinic acid 3,7-dimethyl-octa-2,6-dienyl ester 3-(3-isopropyl-phenyl)-but-1-enyl ester According to the same procedure, succinic acid 3,7-dimethyl-octa-2,6-dienyl ester 3-(3-isopropyl-phenyl)-but-1-enyl ester was prepared from acetic acid 3-(3-isopropyl-phenyl)-but-1-enyl ester, 3-chlorocarbonyl-propionic acid 3,7-dimethyl-oct-2,6-dienyl ester and potassium tert-butoxide.

e) Succinic acid 3-(3-isopropyl-phenyl)-but-1-enyl ester phenethyl ester

According to the same procedure, succinic acid 3-(3-isopropyl-phenyl)-but-1-enyl ester phenethyl ester was prepared from acetic acid 3-(3-isopropyl-phenyl)-but-1-enyl ester, 3-chlorocarbonyl-propionic acid phenethyl ester and potassium tert-butoxide.

f) Succinic acid 3-(4-tert-butyl-phenyl)-2-methyl-propenyl ester 3,7-dimethyl-octa-2,6-dienyl ester According to the same procedure, succinic acid 3-(4-tert-butyl-phenyl)-2-methyl-propenyl ester 3,7-dimethyl-octa-2,6-dienyl ester was prepared from acetic acid 3-(4-tert-butyl-phenyl)- 2-methyl-propenyl ester, 3-chlorocarbonyl-propionic acid 3,7-dimethyl-oct-2,6-dienyl ester and potassium tert-butoxide.

g) Succinic acid 3-(4-tert-butyl-phenyl)-2-methyl-propenyl ester phenethyl ester According to the same procedure, succinic acid 3-(4-tert-butyl-phenyl)-2-methyl-propenyl ester phenethyl ester was prepared from acetic acid 3-(4-tert-butyl-phenyl)-2-methylpropenyl ester, 3-chlorocarbonyl-propionic acid phenethyl ester and potassium tert-butoxide.

h) Succinic acid 3-(4-tert-butyl-phenyl)-2-methyl-propenyl ester 1,2-dimethyl-4-(2,2,3-trimethyl-cyclopent-3-enyl)-but-3-enyl ester According to the same procedure, succinic acid 3-(4-tert-butyl-phenyl)-2-methyl-propenyl ester 1,2-dimethyl-4-(2,2,3-trimethyl-cyclopent-3-enyl)-but-3-enyl ester was prepared from acetic acid 3-(4-tert-butyl-phenyl)-2-methyl-propenyl ester, 3-chlorocarbonyl-propionic acid 1,2-dimethyl-4-(2,2,3-trimethyl-cyclopent-3-enyl)-but-3-enyl ester, and potassium tert-butoxide.

i) Succinic acid 3,7-dimethyl-octa-2,6-dienyl ester undeca-1,9-dienyl ester

According to the same procedure, succinic acid 3,7-dimethyl-octa-2,6-dienyl ester undeca-1,9-dienyl ester was prepared from acetic acid undeca-1,9-dienyl ester, 3-chlorocarbonyl-propionic acid 3,7-dimethyl-oct-2,6-dienyl ester and potassium tert-butoxide.

j) Succinic acid 3-(4-isopropyl-phenyl)-2-methyl-propenyl ester phenethyl ester

According to the same procedure, succinic acid 3-(4-isopropyl-phenyl)-2-methyl-propenyl ester phenethyl ester was prepared from acetic acid 3-(4-isopropyl-phenyl)-2-methyl-propenyl ester, 3-chlorocarbonyl-propionic acid phenethyl ester and potassium tert-butoxide.

k) Succinic acid 3,7-dimethyl-oct-6-enyl ester 3-(4-isopropyl-phenyl)-2-methyl-propenyl ester According to the same procedure, succinic acid 3,7-dimethyl-oct-6-enyl ester 3-(4-isopropyl-phenyl)-2-methyl-propenyl ester was prepared from acetic acid 3-(4-isopropyl-phenyl)-2-methyl-propenyl ester, 3-chlorocarbonyl-propionic acid 3,7-dimethyl-oct-6-enyl ester and potassium tert-butoxide.

l) Succinic acid 3,7-dimethyl-oct-6-enyl ester 2,6,10-trimethyl-undeca-1,9-dienyl ester According to the same procedure, succinic acid 3,7-dimethyl-oct-5-enyl ester 2,6,10-trimethyl-undeca-1,9-dienyl ester was prepared from acetic acid 2,6,10-trimethyl-undeca-1,9-dienyl ester, 3-chlorocarbonyl-propionic acid 3,7-dimethyl-oct-6-enyl ester and potassium tert-butoxide.

m) Succinic acid 2,6-dimethyl-hepta-1,5-dienyl ester 3,7-dimethyl-octa-2,6-dienyl ester According to the same procedure, succinic acid 2,6-dimethyl-hepta-1,5-dienyl ester 3,7-dimethyl-octa-2,6-dienyl ester was prepared from acetic acid 2,6-dimethyl-hepta-1,5-dienyl ester, 3-chlorocarbonyl-propionic acid 3,7-dimethyl-oct-2,6-dienyl ester and potassium tert-butoxide.

n) Succinic acid hex-3-enyl ester 3-methoxycarbonyl-methyl-2-pentyl-cyclopent-1-enyl ester According to the same procedure, succinic acid hex-3-enyl ester 3-methoxycarbonyl-methyl-2-pentyl-cyclopent-1-enyl ester was prepared from 3-oxo-2-pentyl-cyclopentane acetic acid methyl ester, 3-chlorocarbonyl-propionic acid hex-3-enyl ester and potassium tert-butoxide.

o) Succinic acid 3,7-dimethyl-oct-6-enyl ester 3-methoxycarbonyl-methyl-2-pentyl-cyclopent-1-enyl ester According to the same procedure, succinic acid 3,7-dimethyl-oct-6-enyl ester 3-methoxycarbonyl-methyl-2-pentyl-cyclopent-1-enyl ester was prepared from 3-oxo-2-pentyl-cyclopentane acetic acid methyl ester, 3-chlorocarbonyl-propionic acid 3,7-dimethyl-oct-6-enyl ester and potassium tert-butoxide.

EXAMPLE 7

Succinic acid 3-(4-tert-butyl-phenyl)-2-methyl-propenyl ester methyl ester

An alternative method to prepare this compound is as follows. To 4.06 g (0.1015 M) NaH (60%) suspended in 90 ml THF were added slowly 10.26 g (0.138 M) tert-butanol. After the evolution of hydrogen ceased, the flask was cooled to −20° C. 18.86 g (0.0923 M) 2-methyl-3-(4-tert-butylphenyl) propanal was then added over 15 minutes at −20° to −15° C. After 5 minutes further stirring this turpid solution was added over 16 minutes to 13.9 g (0.0923 M) 3-carbomethyoxypropionly chloride in 45 ml THF at −15° C. After 10 minutes, 200 ml ether was added and the solution was washed three times with water. The organic phase was then dried, filtered and evaporated to dryness. The residue was purified by distillation without column. The material boiling at 171°–181° C./0.2 Torr was collected to yield 20.38 g (purity GC: 91%).

NMR (CDCl$_3$) δ 7.36–7.22 (m, 2H), 7.17–6.96 (m, 3H), 3.71 (s, 3H), 3.43/3.21 (s, E/Z), 2H), 2.82–2.61 (m, 4H), 1.61 (s, 3H), 1.31 s, 9H) ppm.

The compounds of the above examples are precursors for organoleptic compounds. Those of Examples 2a, o, p and q are also precursors for antimicrobial compounds.

EXAMPLE 8

Test cloth was washed with a lipase-containing detergent to which one or more of the precursors of Examples 2, 3b, 6 and 7 had been added. Headspace analysis of the wet and dry laundry indicated the presence of the fragrances. The fragrance level was higher than when the test cloth was washed with a lipase-containing detergent to which one or more fragrances were added.

EXAMPLE 9

Test cloth was washed with a lipase-containing detergent and then a fabric softener, containing one or more of the precursors of Examples 2, 3b, 6 and 7 was added to the rinse cycle. Headspace analysis of the wet and dry laundry indicated the presence of the fragrances. The fragrance level was higher than when the test cloth was washed with a lipase-containing detergent and then a fabric softener, containing one or more fragrances, was added to the rinse cycle.

EXAMPLE 10

Axilla bacteria cultures containing 0.1% of one or more of the precursors of Examples 2, 3b, 6 and 7 were incubated for 20 hours at 30° C. After filtration from the cells, the presence of the corresponding fragrance was in each case detected by headspace-GC techniques and/or the majority of an 18 member panel.

The same tests were carried out with inactivated cultures (85°/20 min). The odor of the corresponding fragrance could not be detected after incubation, excluding therefore a hydrolysis by the medium or the culture.

EXAMPLE 11

The following set forth examples for the use of the compounds of the present invention in various products. The methods of forming the following compositions are well known to those skilled in the art. All formulations may contain additional ingredients known to those skilled in the art, e.g. colorants, opacifiers, buffers, antioxidants, vitamins, emulsifiers, UV absorbers, silicones and the like. All products can also be buffered to the desired pH. All values are % w/w. Delayed Release Fragrances stands in the following for compounds of Examples 2, 3b, 6 and 7.

| a) Deo-colognes | A | B | C | D |
|---|---|---|---|---|
| Delayed Release Fragrances | 0.5 | 1.5 | 2.5 | 6.0 |
| Fragrance | 0.5 | 1.5 | 2.5 | 6.0 |
| Triclosan (Ciba Geigy) | 1.0 | — | 0.75 | 1.0 |
| Alcohol to | 100 | 100 | 100 | 100 |

| b) Deo-Sticks | |
|---|---|
| Antiperspirant | |
| Ethylene Glycol Monostearate | 7.0 |
| Shea butter | 3.0 |
| Neobee 1053 (PVO International) | 12.0 |
| Generol 122 (Henkel) | 5.0 |
| Kesscowax B (Akzo) | 17.0 |
| Dimethicone Dow Corning 345 | 35.0 |
| Aluminum Sesquichlorhydrate | 20.0 |
| Delayed Release Fragrances | 0.5 |
| Fragrance | 0.5 |
| Antiperspirant | |
| Steary Alcohol | 17.0 |
| Castor Wax | 3.0 |
| Talc | 5.0 |
| Aluminum Zirconium Tetrachlor-hydrate | 20.0 |
| Delayed Release Fragrances | 1.0 |
| Fragrance | 1.0 |
| Dimethicone Dow 245 to | 100.0 |
| Clear Deodorant Stick | |
| Witconol APM | 44.0 |
| Propylene Glycol | 20.0 |
| Alcohol 39C | 20.0 |
| Demin water | 7.0 |
| Monamid 150ADD | 5.0 |
| Millithix 925 | 2.0 |
| Ottasept Extra | 0.5 |
| Delayed Release Fragrances | 0.75 |
| Fragrance | 0.75 |
| Deodorant Stick | |
| Propylene Glycol | 69.0 |
| Demin Water | 21.8 |
| Triclosan | 0.2 |
| Sodium Stearate | 8.0 |
| Delayed Release Fragrances | 0.5 |
| Fragrance | 0.5 |
| Alcohol free Deodorant Stick | |
| PPG-3 Myristyl Ether (Witconol APM) | 36.0 |
| Propylene Glycol | 36.0 |
| Demin Water | 19.0 |
| Triclosan | 0.25 |
| Sodium Stearate | 7.75 |
| Delayed Release Fragrances | 0.5 |
| Fragrance | 0.5 |

| c) Antiperspirant Aerosol | |
|---|---|
| Absolute Ethanol | 15.0 |
| Zirconium Aluminum tetrachlor-hydrate | 5.0 |
| Bentone 38 | 1.5 |
| Delayed Release Fragrances | 0.75 |
| Fragrance | 0.75 |
| S-31 Hydocarbon propellant to | 100.0 |

| d) Antiperspirant Pump | |
|---|---|
| Demin water | 57.5 |
| Aluminum Sesquichlorhydrate | 20.0 |
| Triton X-102 (Union Carbide) | 2.0 |
| Dimethyl Isosorbide (ICI) | 20.0 |
| Delayed Release Fragrances | 0.25 |
| Fragrance | 0.25 |

| e) Roll-On | |
|---|---|
| Dimethicone DC 354 (Dow Corning) | 69.0 |
| Bentone 38 | 10.0 |
| Rezal 36 GP (Reheis Chem. Co.) | 20.0 |
| Delayed Release Fragrances | 0.5 |
| Fragrance | 0.5 |

In the above examples, the following components were used:

| | |
|---|---|
| Triclosan | 5-chloro-2-(2,4-dichloro-phenoxy)phenol |
| Neobee 1053 | glycerol tricaprate/caprylate |
| Generol 122 | soya sterol |
| Kesscowax B | cetyl alcohol and glycol polymer |
| Witconol APM | polypropylene glycol-3 myristyl ether |
| Monamid 150 ADD | cocoamide diethanolamine |
| Millithix 925 | dibenzylidene sorbitol |
| Ottasept Extra | quaternium 18 hectorite |
| Bentone 38 | quaternium 18 hectorite |
| Triton X-102 | octoxynol-13 |
| Dimethicone DC 354 | mixture of fully methylated linear siloxanepolymers end-blocked with trimethylsiloxy units |
| Rezal 36 GP | Aluminium zirconium tetra-chlorohydrexglycine |

EXAMPLE 12 a) Fabric softener of the ester quat type (4×concentrate):

| INGREDIENTS | CHEMICAL NAME | % |
|---|---|---|
| PHASE A | | |
| DEIONISED WATER to | | 100.0 |
| MgCl$_2$ (saturated sol.) | Magnesium chloride | 1.0 |

-continued

| INGREDIENTS | CHEMICAL NAME | % |
|---|---|---|
| PHASE B | | |
| REWOQUAT WE 18 | Di-(tallow carboxyethyl)hydroxy ethyl methylammonium methosulfate | 15.0 |
| GENAPOL O 100 | Ethoxylated fatty alcohol C16–C18 10EO | 2.0 |
| ANTIFOAM DB 31 | | 0.5 |
| PHASE C | | |
| ISOPROPYL ALCOHOL | | 3.0 |
| PRESERVATIVE | | Qs |
| PERFUME | | Qs |

PROCESS:

While stirring and heating to 65° C., mix part A, then part B preheated to 65° C. After cooling to room temperature, add part C.

The pH value of the finished product is 2.60.

Recommended level of perfume is 1.0%. Delayed release fragrances from Examples 2, 3b, 6 and 7 may be any part of this 1.0%.

b) Fabric softener of the ester quat type (1×concentrate):

| INGREDIENTS | CHEMICAL NAME | % |
|---|---|---|
| PHASE A | | |
| DEIONISED WATER to | | 100.0 |
| PHASE B | | |
| REWOQUAT WE 18 | Di-(tallow carboxyethyl)hydroxy ethyl methylammonium methosulfate | 6.0 |
| DOBANOL 25-9 | Ethoxylated fatty alcohol C12–C15 9EO | 0.50 |
| ANTIFOAM DB 31 | | 0.10 |
| PHASE C | | |
| MYACIDE BT 30 | 2-bromo-2-nitropropane 1,3 diol | 0.03 |
| PROXEL GXL | Benzisothiazolinone sodium salt | 0.02 |
| PERFUME | | Qs |

PROCESS:

While stirring and heating to 65° C., mix part A, then part B preheated to 65° C. After cooling to room temperature, add part C.

The pH value of the finished product is 3.50.

Recommended level of perfume: 0.3%. Delayed release fragrances from Examples 2, 3b, 6 and 7 may be any part of this 0.3%.

What is claimed is:

1. A compound of the formula I:

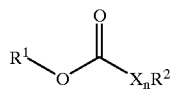

wherein

R¹ is the residue of the enol form of an aldehyde having 7 or more carbon atoms or a ketone having 8 or more carbon atoms, X is a saturated bivalent hydrocarbon residue with a straight chain with 1 or 2 carbon atoms or a phenyl ring, R² is a saturated or unsaturated, substituted or unsubstituted carbocyclic or heterocyclic residue or —COOY, wherein Y is a metal atom or R³, and R³ is the residue of an alcohol or phenol or has the same definition as R¹ and is the same or different as R¹, n is 0 or 1, wherein if R¹ is a 3-phenyl propanal derivative optionally substituted by a methyl group in position 2, the phenyl ring has at least one substituent, and if R¹ is a 2-phenyl ethanal derivative, the phenyl ring has at least one substituent.

2. A method for producing one or more organoleptic compounds comprising contacting a compound of formula I:

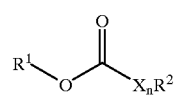

with skin bacteria, enzymes, elevated temperature or by acidic or alkaline pH values to cleave the compound of formula I, wherein R¹ is the residue of the enol form of an aldehyde having 7 or more carbon atoms or a ketone having more than 8 carbon atoms, X is a saturated bivalent hydrocarbon residue with a straight chain with 1 or 2 carbon atoms or a phenyl ring, R² is a saturated or unsaturated, substituted or unsubstituted carbocyclic or heterocyclic residue or —COOY, wherein Y is a metal atom or R³, and R³ is the residue of an alcohol or phenol or has the same definition as R¹ and is the same or different as R¹, n is 0 or 1, wherein if R¹ is a 3-phenyl propanal derivative optionally substituted by a methyl group in position 2, the phenyl ring has at least one substituent, and if R¹ is a 2-phenyl ethanal derivative, the phenyl ring has at least one substituent.

3. The method according to claim 2, wherein the enzymes are protease or lipase.

4. A fragrance precursor composition comprising a compound according to claim 1.

5. In an organoleptic composition, the improvement including a compound according to claim 1, as a precursor for an organoleptic masking agent.

6. Compounds according to claim 1, wherein the substituents R¹ and R³ are different.

7. Compounds of claim 1, wherein R¹ and R³ are the same.

8. Compounds according to claim 1, wherein the heteroatoms in X are O, N, S and/or P.

9. Compounds according to claim 1, wherein R³ is the residue of an organoleptic alcohol or phenol.

10. Compounds according to claim 1, wherein R² represents a substituted or unsubstituted aromatic residue.

11. Compounds according to claim 1, said compounds being of the formula II (II)

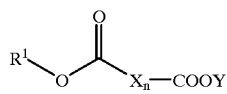

preferably of formula III (III)

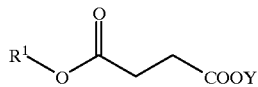

wherein $R^1$, X, Y and n have the same meaning as in claim 1.

12. Compounds according to claim 1, said compounds being of formula IV (IV)

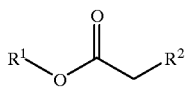

wherein $R^1$ has the same meaning as in claim 1 and $R^2$ represents a saturated or unsaturated, substituted or unsubstituted carbocyclic or heterocyclic residue.

13. Compounds according to claim 1, said compounds being of formula V (V)

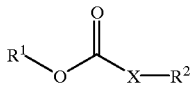

wherein $R^1$ has the same meaning as in claim 1, $R^2$ is hydrogen and X represents a saturated or unsaturated bivalent hydrocarbon residue with straight or branched chain with 1 to 20 carbon atoms and substituted by —OH.

14. A compound according to claim 1 which is phenyl-acetic acid 3-(4-tert-butyl-phenyl)-2-methyl-propenyl ester.

15. A compound according to claim 1 which is selected from the group consisting of:

a) succinic acid methyl ester undeca-1,9-dienyl ester;
b) succinic acid 3-(4-tert-butyl-phenyl)-2-methyl-propenyl ester methyl ester;
c) phenyl-acetic acid 2-methyl-undec-1-enyl ester;
d) phenyl-acetic acid undeca-1,9-dienyl ester;
e) phenyl-acetic acid 2,4-dimethyl-cyclohex-3-enylidenemethyl ester;
f) (4-methoxy-phenyl)-acetic acid 3-(4-tert-butyl-phenyl)-2-methyl-propenyl ester;
g) 3-phenyl-propionic acid undeca-1,9-dienyl ester;
h) 3-phenyl-propionic acid 2,4-dimethyl-cyclohex-3-enylidene-methyl ester;
i) 3-phenyl-propionic acid 3-(4-tert-butyl-phenyl)-2-methyl-propenyl ester;
j) 4-methoxy-benzoic acid 2-methyl-undec-1-enyl ester;
k) 4-methoxy-benzoic acid 2,4-dimethyl-cyclohex-3-enylidenemethyl ester;
l) 4-methoxy-benzoic acid 3-(3-isopropyl-phenyl)-but-1-enyl ester;
m) 4-methoxy-benzoic acid undeca-1,9-dienyl ester;
n) succinic acid bis-[3-(4-tert-butyl-phenyl)-2-methyl-propenyl] ester;
o) succinic acid bis-[3-(3-isopropyl-phenyl)-but-1-enyl] ester;
p) succinic acid 3,7-dimethyl-oct-6-enyl ester 3-(3-isopropyl-phenyl)-but-1-enyl ester;
q) succinic acid 3-(4-tert-butyl-phenyl)-2-methyl-propenyl ester 3,7-dimethyl-oct-6-enyl ester;
r) succinic acid 3,7-dimethyl-oct-6-enyl ester undeca-1,9-dienyl ester;
s) 3-phenyl-acrylic acid 3-(4-tert-butyl-phenyl)-2-methyl-propenyl ester;
t) succinic acid 3-(3-isopropyl-phenyl)-but-1-enyl ester methyl ester;
u) succinic acid 3-methoxycarbonylmethyl-2-pentyl-cyclopent-1-enyl ester methyl ester;
v) succinic acid 3-(4-isopropyl-phenyl)-2-methyl-propenyl ester methyl ester;
w) phenyl acetic acid 3-(4-isopropyl-phenyl)-2-methyl-propenyl ester;
x) phenyl acetic acid 3-methoxy carbonyl methyl-2-pentyl-cyclopent-1-enyl ester;
y) phenyl acetic acid 3-(3-isopropyl-phenyl)-but-1-enyl ester;
z) (4-methoxy-phenyl)-acetic acid 3-(3-isopropyl-phenyl)-but-1-enyl ester;
aa) 3-phenyl-propionic acid 3-(3-isopropyl-phenyl)-but-1-enyl ester;
bb) 4-methoxy-benzoic acid 3-(4-tert-butyl-phenyl)-2-methyl-propenyl ester;
cc) succinic acid bis-[3-(4-isopropyl-phenyl)-2-methyl-propenyl] ester;
dd) succinic acid bis-(2,6,10-trimethyl-undeca-1,9-dienyl) ester;
ee) succinic acid bis-(2,6-dimethyl-hepta-1,5-dienyl) ester;
ff) succinic acid bis-[2-(3,7-dimethyl-oct-6-enyloxy)-vinyl] ester;
gg) terephthalic acid bis-[3-(4-tert-butyl-phenyl)-2-methyl-propenyl] ester;
ii) succinic acid 3,7-dimethyl-octa-2,6-dienyl ester 3-(3-isopropyl-phenyl)-but-1-enyl ester;
jj) succinic acid 3-(3-isopropyl-phenyl)-but-1-enyl ester phenethyl ester;
kk) succinic acid 3-(4-tert-butyl-phenyl)-2-methyl-propenyl ester 3,7-dimethyl-octa-2,6-dienyl ester;
ll) succinic acid 3-(4-tert-butyl-phenyl)-2-methyl-propenyl ester phenethyl ester;
mm) succinic acid 3-(4-tert-butyl-phenyl)-2-methyl-propenyl ester 1,2-dimethyl-4-(2,2,3-trimethyl-cyclopent-3-enyl)-but-3-enyl ester;
nn) succinic acid 3,7-dimethyl-octa-2,6-dienyl ester undeca-1,9-dienyl ester;
oo) succinic acid 3-(4-isopropyl-phenyl)-2-methyl-propenyl ester phenethyl ester;
pp) succinic acid 3,7-dimethyl-oct-6-enyl ester 3-(4-isopropyl-phenyl)-2-methyl-propenyl ester;
qq) succinic acid 3,7-dimethyl-oct-6-enyl ester 2,6,10-trimethyl-undeca-1,9-dienyl ester;

rr) succinic acid 2,6-dimethyl-hepta-1,5-dienyl ester 3,7-dimethyl-octa-2,6-dienyl ester;

ss) succinic acid hex-3-enyl ester 3-methoxycarbonyl-methyl-2-pentyl-cyclopent-1-enyl ester;

tt) succinic acid 3,7-dimethyl-oct-6-enyl ester 3-methoxycarbonyl-methyl-2-pentyl-cyclopent-1-enyl ester; and uu) phenyl-acetic acid 3-(4-tert-butyl-phenyl)-2-methyl-propenyl ester.

16. A personal care product comprising a compound of claim 1.

17. A laundry product comprising a compound of claim 1.

* * * * *